US007250506B2

(12) United States Patent
Baumann et al.

(10) Patent No.: US 7,250,506 B2
(45) Date of Patent: Jul. 31, 2007

(54) OLIGONUCLEOTIDES AND METHODS FOR DETECTING HEPATITIS C VIRAL NUCLEIC ACIDS

(75) Inventors: Russell Baumann, Rancho Santa Margarita, CA (US); Hasnah Hamdan, Riverside, CA (US); Michael Lewinski, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 373 days.

(21) Appl. No.: 10/759,514

(22) Filed: Jan. 16, 2004

(65) Prior Publication Data
US 2006/0134632 A1    Jun. 22, 2006

Related U.S. Application Data

(63) Continuation of application No. 10/011,855, filed on Dec. 4, 2001, now Pat. No. 6,946,245.

(51) Int. Cl.
*C07H 21/04* (2006.01)
*C12P 19/34* (2006.01)
(52) U.S. Cl. ............... 536/24.3; 536/24.31; 536/24.32; 536/24.33; 435/91.2
(58) Field of Classification Search ..................... None
See application file for complete search history.

(56) References Cited

U.S. PATENT DOCUMENTS

| 4,868,105 | A |   | 9/1989  | Urdea et al. ............ 435/6   |
|-----------|---|---|---------|----------------------------------|
| 5,527,669 | A |   | 6/1996  | Resnick et al. .......... 435/5  |
| 5,538,848 | A |   | 7/1996  | Livak et al. ............ 435/5  |
| 5,635,352 | A | * | 6/1997  | Urdea et al. ............ 435/6  |
| 5,681,697 | A | * | 10/1997 | Urdea et al. ............ 435/6  |
| 5,691,146 | A |   | 11/1997 | Mayrand ................ 435/6   |
| 5,723,591 | A |   | 3/1998  | Livak et al. ........... 536/22.1|
| 5,736,333 | A |   | 4/1998  | Livak et al. ............ 435/6  |
| 5,837,442 | A |   | 11/1998 | Tsang .................... 435/5 |
| 5,866,336 | A |   | 2/1999  | Nazarenko et al. ....... 435/6   |
| 5,876,930 | A |   | 3/1999  | Livak et al. ............ 435/6  |
| 5,952,202 | A |   | 9/1999  | Aoyagi et al. ......... 435/91.2 |
| 6,028,290 | A |   | 2/2000  | Yashuhara et al. ..... 219/130.1 |
| 6,030,787 | A |   | 2/2000  | Livak et al. ............ 435/6  |
| 6,060,240 | A |   | 5/2000  | Kamb et al. ............. 435/6  |
| 6,150,107 | A |   | 11/2000 | Glazer et al. ............ 435/6 |
| 6,258,569 | B1|   | 7/2001  | Livak et al. ........... 435/91.1|
| 6,297,016 | B1|   | 10/2001 | Egholm et al. ............ 435/6 |
| 6,316,230 | B1|   | 11/2001 | Egholm et al. ......... 435/91.1 |
| 6,316,610 | B2|   | 11/2001 | Lee et al. .............. 536/23.1|

FOREIGN PATENT DOCUMENTS

EP    0529493 B1    12/1997
JP    103899-A/10    *  4/1999

OTHER PUBLICATIONS

AF 059603 published on NCBI. pp. 1-2.*

Beames et al., "Development of a Primary Tamarin Hepatocyte Culture System for GB Virus-B: A Surrogate Model for Hepatitis C Virus," Journal of Virology, 74(24):11764-11772, 2000.

Bukh et al., "Sequence Analysis of the 5' Noncoding Region of Hepatitis C Virus," Proc. Natl. Acad. Sci. USA, 89:4942-4946, 1992.

Chu et al., "Postsynthesis Functionalization of Oligonucleotides," Methods in Molecular Biology, 26:145-165, 1994.

Henning et al., "A Novel RT-PCR for Reliable and Rapid HCV RNA Screening of Blood Donations," Transfusion, 41:1100-1106, 2001.

Hileman et al., "Synthesis and Characterization of Conjugates Formed Between Periodate-Oxidized Ribonucleotides and Amine-Containing Fluorophores," Bioconjugate Chem., 5:436-444, 1994.

Kawai et al., "Quantification of Hepatitis C Virus by TaqMan PCR: Comparison with HCV Amplicor Monitor Assay," Journal of Medical Virology, 58:121-126, 1999.

Kleiber et al., "Performance Characteristics of a Quantitative, Homogeneous TaqMan RT-PCR Test for HCV RNA," Journal of Molecular Diagnostics, 2(3)158-166, 2000.

Komurian-Pradel et al., "Quantitation of HCV RNA Using Real-Time PCR and Fluorimetry," Journal of Virological Methods, 95:111-119, 2001.

Landegren et al., "DNA Diagnostics-Molecular Techniques and Automation," Science, 242:229, 1998.

Martell et al., "High-Throughput Real-Time Reverse Transcription-PCR Quantitation of Hepatitis C Virus RNA," Journal of Clinical Microbiology, 37(2)327-332, 1999.

Matthews et al., "Analytical Strategies for the Use of DNA Probes," Analytical Biochemistry, 169-1-25, 1988.

Meng et al., "Automated Multiplex Assay System for Simultaneous Detection of Hepatitis B Virus DNA, Hepatitis C Virus RNA, and Human Immunodeficiency Virus Type 1 RNA," Journal of Clinical Microbiology, 2937-2945, 2001.

Mercier et al., "Simultaneous Screening for HBV DNA and HCV RNA Genomes in Blood Donations Using A Novel TaqMan PCR Assay," Journal of Virological Methods, 77:1-9, 1999.

Theodore E. Millfin, "Use and Applications of Nucleic Acid Probes in the Clinical Laboratory," Clinical Chemistry, 35(9):1819-1825, 1989.

Morris et al., "Rapid Reverse Transcription-PCR Detection of Hepatitis C Virus RNA in Serum by Using the TaqMan Fluorogenic Detection System," Journal of Clinical Microbiology, 34(12):2933-2936, 1996.

(Continued)

*Primary Examiner*—Bruce Campell
*Assistant Examiner*—Bao Qun Li
(74) *Attorney, Agent, or Firm*—Foley & Lardner LLP

(57) ABSTRACT

The present invention provides methods and compositions for determining the presence and/or amount of HCV nucleic acids in a test sample. In particular, substantially purified oligonucleotide primers and probes are described that can be used for qualitatively and quantitatively detecting HCV nucleic acid in a test sample by amplification methods. The present invention also provides primers and probes for generating and detecting control nucleic acid sequences that provide a convenient method for assessing internal quality control of the HCV assay.

7 Claims, No Drawings

OTHER PUBLICATIONS

Petrik et al., "High Throughput PCR Detection of HCV Based on Semiautomated Multisample RNA Capture," Journal of Virological Methods, 64:147-159, 1997.

Randall Saiki, "Amplification of Genomic DNA," PCR Protocols: A Guide to Methods and Applications, Academic Press, Ch. 2, p. 13-20, 1990.

Van Schie et al., "Semiautomated Clone Verification by Real-Time PCR Using Molecular Beacons," BioTechniques, 29:1296-1308, 2000.

Wharam et al., "Specific Detection of DNA and RNA Targets Using a Novel Isothermal Nucleic Acid Amplification Assay Based on the Formation of a Three-Way Junction Structure," Nucleic Acids Research, 29(11):1-8, 2001.

Hafner et al., "Isothermal Amplification and Multimerization of DNA by *Bst* DNA Polymerase," BioTechniques, 30:825-867, 2001.

Young et al., "Detection of Hepatitis C Virus RNA by a Combined Reverse Transcription-Polymerase Chain Reaction Assay," Journal of Clinical Microbiology, 31(4):882-886, 1993.

Young et al., "Detection of Hepatitis C Virus RNA by a Combined Reverse Transcription PCR Assay: Comparison with Nested Amplification and Antibody Testing," Journal of Clinical Microbiology, 33(3):654-657, 1995.

\* cited by examiner

OLIGONUCLEOTIDES AND METHODS FOR DETECTING HEPATITIS C VIRAL NUCLEIC ACIDS

CROSS-REFERENCE TO RELATED PATENT APPLICATIONS

This application is a Continuation of U.S. application Ser. 10/011,855, filed Dec. 4, 2001, now U.S. Pat. No. 6,946,245 incorporated herein by reference in its entirety.

FIELD OF THE INVENTION

The present invention relates generally to compositions and methods for quantitatively and qualitatively detecting hepatitis C viral nucleic acids in a test sample.

BACKGROUND OF THE INVENTION

The following discussion of the background of the invention is merely provided to aid the reader in understanding the invention and is not admitted to describe or constitute prior art to the present invention.

One of the major causes of hepatitis are specific hepatitis viruses. Among them, HCV is now known to cause most cases of what was previously termed non-A, non-B (NANB) hepatitis, and causes the vast majority of post-transfusion and sporadic NANB hepatitis. HCV infections is generally symptomatically mild. However, at least half of all infected individuals appear to develop chronic hepatitis, and 20% of these may develop cirrhosis.

HCV is a small RNA virus containing a single molecule of RNA of about 10,000 nucleotides in length. The genome of HCV contains a single, long, open reading frame (ORF) that is translated into a single, large polyprotein and subsequently processed, and exhibits a large degree of nucleic acid sequence heterogeneity. The entire genome of HCV has been cloned and sequenced. To date, at least five related genotypes of the virus have been found. The relative abundance of each genotype throughout the world is the subject of intensive study. The 5' untranslated region (UTR) of the virus is remarkably well conserved and has provided an excellent site for oligonucleotide probes and primers (Bukh et al., Proc. Natl. Acad. Sci USA 88:942-946, 1992).

Since multiple HCV subtypes exist with varying amino acid sequences, these subtypes vary geographically and play a role in disease virulence. HCV can also alter its amino acid pattern over time in an infected person, hampering vaccine development. Since most cases of hepatitis C are subclinical, even in the acute stage, hepatitis C is often uncovered by the serendipitous detection of anti-HCV in apparently healthy persons.

HCV causes at least 80% of post-transfusion hepatitis cases and a substantial proportion of sporadic acute hepatitis cases. It is also implicated in many cases of chronic hepatitis, cryptogenic cirrhosis, and hepatocellular carcinoma unrelated to HBV. Infection is most commonly acquired via blood, either from transfusion or IV drug use. Sexual transmission and vertical transmission from mother to infant can occur but are relatively rare. A small proportion of seemly healthy persons are chronic HCV carriers, who often have subclinical chronic hepatitis or even cirrhosis. HCV is associated with many disorders including "immune" disorders, such as glomerulonephritis.

Diagnosis of hepatitis C is based on the presence of serum antibody (anti-HCV), which is not protective and implies active infection. First generation serologic tests were often falsely positive, but second and third generation tests are more reliable. Anti-HCV often appears several weeks after acute infection, so a negative test does not exclude recent infection.

The measurement of HCV nucleic acid in serum has become an important tool to identify individuals with high viral replication, to monitor patients on therapy, and to predict whether antiviral therapy will be successful.

Several tests have been employed to detect HCV in serum and other body fluids. Hybridization assays for detecting HCV polynucleotides are known in the art. For example, Matthews and Kricka, Analytical Biochemistry 169:1, 1988; Landegren et al., Science 242:229, 1988; Mattlin, *Clinical Chem.* 35: 1819, 1989; and U.S. Pat. No. 4,868,105.

To increase the sensitivity of such assays, HCV nucleic acid sequences can be detected by reverse transcribing HCV genomic RNA to form cDNA, amplifying the resulting cDNA by, for example, the polymerase chain reaction (PCR), and detecting the presence of amplified product. The HCV detection assays based on PCR amplification of HCV polynucleotide sequences were described in U.S. Pat. No. 5,527,669; European Patent Publication No. 529,493; Young et al., *J. Clin. Microbiol.* 31(4): 882-886, 1993; and Young et al., *J. Sin. Microbiol.* 33(3): 654-657, 1995. Therefore, when active disease is suspended or post-treatment follow up is desired, detection of HCV-RNA by PCR provides a sensitive technique for the direct detection of HCV-RNA in patient serum.

Because of the sequence heterogeneity among HCV strains, there is still a need for primer oligonucleotides for amplifying HCV sequences, each chosen from a conserved region so that all, or almost all, strains will be amplified. U.S. Pat. No. 5,837,442, which is incorporated herein by reference, provides primers for the amplification of HCV nucleic acid with significantly high efficiency. This patent provides that amplification of HCV RNA can be carried out using a combined reverse transcription-polymerase chain reaction (RT-PCR) amplification, in which a single enzyme catalyzes the primer extension both from the initial genomic RNA template (i.e. reverse transcription) and from the DNA templates synthesized in the amplification process.

Hybridization assays for detection of nucleic acids are described in, for example, U.S. Pat. Nos. 6,258,569; 6,030,787; 5,952,202; 5,876,930; 5,866,336; 5,736,333; 5,723,591; 5,691,146; and 5,538,848. Publications for detection of HCV using Real-time PCR (Taqman systems) include the following: Henning et al., Transfusion 41(9): 1100-6, 2001; Meng et al., J. Clin. Microbiol. 39(8): 2937-45, 2001; Komurian et al., J. Virol Methods 95(1-2): 111-9, 2000 Kleiber et al., J. Mol. Diagn 2(3): 158-66, 2000; Beames et al., J. Virol. 74(24): 11764-72, 2000 Kawai et al., J. Med. Virol. 58(2): 121-6, 1999; Mercier et al., J. Virol Methods 77(1): 1-9, 1999 Martell et al., J. Clin. Microbiol. 37(2): 327-32, 1999; Petrik et al., J. Virol Methods 64(2: 147-59, 1997; and Morris et al., *J. Clin. Microbiol.* 34(12): 2933-6, 1996.

SUMMARY OF THE INVENTION

The present invention provides methods and compositions for determining the presence and/or amount of HCV nucleic acids in a test sample. In particular, substantially purified oligonucleotides for qualitatively and quantitatively detecting HCV nucleic acids in a test sample by amplification methods are described herein. The present invention can provide a specific, sensitive method that exhibits a broad dynamic range of detection of HCV nucleic acids, and which can advantageously provide quantitative as well as qualitative results.

In various embodiments of the present invention, oligonucleotide primers and probes are used in the methods described herein to provide the HCV assay. Thus, in certain embodiments, the invention relates to primer sequences that can be used to amplify HCV and/or control nucleic acid sequences present in a sample. In certain embodiments, primer sequences can also be used to amplify one or more control nucleic acid sequences, while in other embodiments, primer sequences simultaneously introduce HCV and T7 RNA polymerase promoter sequences into the control amplicon produced. By introducing T7 promoter sequences into the control amplicon, the amplicon can be transcribed into an RNA molecule which is subsequently purified from its DNA predecessor. By introducing HCV sequences into the control amplicon and ultimately into the control RNA, the control can be introduced into test samples, reverse transcribed and amplified by the same primers used to reverse transcribe and amplify the target HCV sequences, providing a convenient positive control.

In additional embodiments, the invention relates in part to probe nucleic acids that can be conjugated to a detectable label, preferably, a fluorescent dye, and most preferably a dye pair located at the 5' and 3' end of the oligonucleotides. Certain labeled oligonucleotides are described that hybridize to amplified HCV nucleic acids, if present, in the sample. Similarly, certain labeled oligonucleotides are described that hybridize to a control amplicon that may have been introduced into the test sample as a positive control.

In a first aspect, the invention relates to a composition of one or more substantially purified oligonucleotides having sequences selected from the following group:

5'-GCA GAA AGC GTC TAG CCA TGG CGT-3' (SEQ ID NO:1), an HCV sequence;

5'-CTC GCA AGC ACC CTA TCA GGC AGT-3' (SEQ ID NO:2), an HCV sequence;

5'-CCG GGA GAG CCA TAG TGG TCT GCG-3' (SEQ ID NO:3), an HCV sequence;

5'-TAA TAC GAC TCA CTA TAG GGG CAG AAA GCG TCT AGC CAT GGC GTA AAA TCC GGT AGT AAC TTG CTA ACC-3' (SEQ ID NO:4), a hybrid nucleic acid comprising HCV, phage lambda, and T7 RNA polymerase promoter sequences;

5'-CTC GCA AGC ACC CTA TCA GGC AGT TAG TGC GGG TGT TGA ATG ATT TCC-3' (SEQ ID NO:5)), a hybrid nucleic acid comprising both HCV and phage lambda sequences; and 5'-TTG GCA ACA GTG GCA TGC ACC G-3' (SEQ ID NO:6), a phage lambda sequence.

In preferred embodiments, one or more of the selected oligonucleotides can be conjugated to a detectable label, preferably a fluorescent dye, and most preferably a dye pair. Particularly preferred oligonucleotide dye conjugates are 5'[2'-chloro-7'-phenyl-1,4-dichloro-6-carboxyfluor (VIC)]-CCG GGA GAG CCA TAG TGG TCT GCG-[6-carboxytetramethylrhodamine (TAMRA)]3' (SEQ ID NO:7); and 5'[6-carboxyfluorescein(FAM)]-TTG GCA ACA GTG GCA TGC ACC G-[6-carboxytetramethylrhodamine (TAMRA)]3' (SEQ ID NO:8). These may be used as probes for HCV and phage lambda, respectively, in methods to detect the presence or amount of specific nucleic acids present in a test sample.

In another aspect, the present invention relates in part to methods that use hybrid HCV-phage lambda and T7 promoter-HCV-phage lambda nucleic acid primers to produce hybrid amplicons comprising a core phage lambda sequence, flanked by HCV sequences and a single T7 RNA polymerase promoter sequence. In preferred embodiments, oligonucleotides having the sequences 5'-TAA TAC GAC TCA CTA TAG GGG CAG AAA GCG TCT AGC CAT GGC GTA AAA TCC GGT AGT AAC TTG CTA ACC-3' (SEQ ID NO:4), and 5'-CTC GCA AGC ACC CTA TCA GGC AGT TAG TGC GGG TGT TGA ATG ATT TCC-3' (SEQ ID NO:5)), are used as primers to amplify a sample of phage lambda nucleic acid to produce the hybrid amplicons.

In certain embodiments, T7-HCV-phage lambda hybrid amplicons can be used to prepare an HCV-phage lambda RNA transcript which is purified for use in HCV assays. In these embodiments, hybrid HCV-phage lambda nucleic acids can be introduced into a sample to be analyzed for the presence or amount of HCV RNA. Because of the flanking HCV sequences present in the hybrid RNA, primers can be selected that can reverse transcribe and amplify both the hybrid nucleic acid added, as well as any HCV present in the sample. Depending on the timing at which the hybrid nucleic acid is introduced into the sample, the hybrid nucleic acid can serve as a positive control for nucleic acid extraction from the sample, and/or for HCV RNA reverse transcription and amplification reactions.

In another aspect, the present invention relates in part to methods for detecting the presence or amount of HCV nucleic acid present in a test sample. These methods preferably comprise amplifying HCV nucleic acids if present in said sample using a pair of oligonucleotide primers; hybridizing said amplified HCV nucleic acids with an oligonucleotide probe; and detecting a signal from said hybridized HCV nucleic acids, wherein the signal is related to the presence or amount of HCV nucleic acids in the test sample.

In various preferred embodiments, the oligonucleotide primers from HCV RNA 5' UTR have the sequences 5'-GCA GAA AGC GTC TAG CCA TGG CGT-3' (SEQ ID NO:1) and 5'-CTC GCA AGC ACC CTA TCA GGC AGT-3' (SEQ ID NO:2); the oligonucleotide probe has the sequence 5'-CCG GGA GAG CCA TAG TGG TCT GCG-3' (SEQ ID NO:3); the oligonucleotide probe comprises a detectable label; the oligonucleotide probe has the sequence 5'(VIC)-CCG GGA GAG CCA TAG TGG TCT GCG-(TAMRA)3' (SEQ ID NO:7); a positive control nucleic acid is introduced into the test sample during the isolation of HCV sequences; the positive control nucleic acid is an HCV-phage lambda hybrid; the positive control nucleic acid is reverse transcribed and amplified by the same primers used to reverse transcribe and amplify the HCV sequences; the positive control nucleic acid is detectable using an oligonucleotide probe having the sequence 5'-TTG GCA ACA GTG GCA TGC ACC G-3' (SEQ ID NO:6); and/or the positive control nucleic acid is detected using an oligonucleotide probe having the sequence 5'(FAM)-TTG GCA ACA GTG GCA TGC ACC G-(TAMRA)3' (SEQ ID NO:8).

In yet another aspect of the present invention, a "real time RT-PCR" assay providing dynamic fluorescence detection of amplified HCV products produced in a RT-PCR amplification reaction using enzyme rTth to reverse transcribe and PCR-amplify HCV RNA is described. During RT-PCR, the amplified products hybridize to probe nucleic acids, which are labeled with both a reporter dye and a quencher dye. When these two dyes are in close proximity, i.e. both are present in an intact probe oligonucleotide, the fluorescence of the reporter dye is suppressed. However, a polymerase, such as rTth, having 5'-3' nuclease activity can be provided in the RT-PCR reaction. This enzyme cleaves the fluorogenic probe if it is bound specifically to the target nucleic acid sequences between the priming sites. The reporter dye and quencher dye are separated upon cleavage, permitting fluorescent detection of the reporter dye. Upon excitation by a laser provided, e.g., by a sequence detection apparatus, the fluorescent signal produced by the reporter dye is detected and/or quantified. The increase in fluorescence is a direct consequence of amplification of target nucleic acids during RT-PCR.

In various preferred embodiments, the oligonucleotide primers used in the RT-PCR amplification have the sequences 5'-GCA GAA AGC GTC TAG CCA TGG CGT-3' (SEQ ID NO:1) and 5'-CTC GCA AGC ACC CTA TCA GGC AGT-3' (SEQ ID NO:2); the reporter dye is VIC and the quencher dye is TAMRA; the HCV oligonucleotide probe has the sequence 5'(VIC)-CCG GGA GAG CCA TAG TGG TCT GCG-(TAMRA)3' (SEQ ID NO:7); a positive control nucleic acid is introduced into the test sample during the isolation of HCV sequences; the positive control nucleic acid is a HCV-phage lambda hybrid; the positive control nucleic acid is reverse transcribed and amplified by the same primers used to reverse transcribe and amplify the HCV sequences; the reporter dye is FAM and the quencher dye is TAMRA; and/or the positive control nucleic acid is detected using an oligonucleotide probe having the sequence 5'(FAM)-TTG GCA ACA GTG GCA TGC ACC G-(TAMRA)3' (SEQ ID NO:8).

In yet another aspect, the methods and compositions for detecting and/or quantifying HCV of the present invention can be used for designing a treatment regimen. In particular, the detection of the presence or amount of HCV nucleic acid in a biological sample following a selected treatment(s) can be used to assess the success or lack thereof in the treatment regimen. The present invention can also be used to compare the relative presence or amount of HCV nucleic acids in a patient before and after such a treatment regimen. Similarly, methods and compositions described herein can be used for screening therapeutic compounds. In particular, the quantitative detection of the presence or amount of HCV nucleic acids in a biological sample following administration of one or more compounds can be used to assess therapeutic efficacy. The present invention can also be used to compare the relative presence or amount of HCV nucleic acids in a patient before and after administration of one or more compounds.

In another aspect, the present invention relates in part to kits comprising sufficient materials for performing one or more methods described herein. In preferred embodiments, a kit includes one or more materials selected from the following group in an amount sufficient to perform at least one HCV assay: Oligonucleotide primers having the sequences 5'-GCA GAA AGC GTC TAG CCA TGG CGT-3' (SEQ ID NO:1) and 5'-CTC GCA AGC ACC CTA TCA GGC AGT-3' (SEQ ID NO:2); an oligonucleotide probe having the sequence 5'-CCG GGA GAG CCA TAG TGG TCT GCG-3' (SEQ ID NO:3); an oligonucleotide probe having the sequence 5'(VIC)-CCG GGA GAG CCA TAG TGG TCT GCG-(TAMRA)3' (SEQ ID NO:7); a positive control nucleic acid to be introduced into a test during the isolation of HCV sequences; a positive control nucleic acid that is a HCV-phage lambda hybrid; a positive control nucleic acid that is detectable using an oligonucleotide probe having the sequence 5'-TTG GCA ACA GTG GCA TGC ACC G-3' (SEQ ID NO:6); a positive control nucleic acid that is detected using an oligonucleotide probe having the sequence 5'(FAM)-TTG GCA ACA GTG GCA TGC ACC G-(TAMRA)3' (SEQ ID. NO:8).

DETAILED DESCRIPTION OF THE PREFERRED EMBODIMENTS

The present invention provides methods and compositions for the rapid, accurate and sensitive determination of HCV nucleic acids in test samples. In particular, oligonucleotide probes and primers are described that can be used in a method for quantitatively or qualitatively detecting HCV nucleic acids in a sample. The present invention also provides primers and probes for generating and detecting control nucleic acid sequences that provide a convenient method for assessing internal quality control of the HCV assay.

As used herein, the term "HCV-phage lambda nucleic acid hybrids" refers to chimeric ribonucleic acid molecules containing both HCV and lambda phage nucleic acids sequences. Preferred HCV-phage lambda hybrids comprise a core sequence from phage lambda, flanked by HCV sequences having sufficient length to hybridize to reverse transcription and amplification primers.

As used herein, the term "purified" in reference to oligonucleotides does not require absolute purity. Instead, it represents an indication that the sequence is relatively more pure than in the natural environment. Such oligonucleotides may be obtained by a number of methods including, for example, laboratory synthesis, restriction enzyme digestion or PCR. A "substantially purified" oligonucleotide is preferably greater than 50% pure, more preferably at least 75% pure, and most preferably at least 95% pure.

As used herein, the term "oligonucleotides" refers to a short polymer composed of deoxyribonucleotides, ribonucleotides or any combination thereof. These oligonucleotides are at least 9 nucleotides in length, preferably 20 to 70 nucleotides long, with 21 to 26 nucleotides being the most common. In certain embodiments, the oligonucleotides are jointed together with a detectable label.

As used herein, the term "HCV nucleic acids" mostly refers to RNA comprising a contiguous sequence from a hepatitis C virus genome, or the complement of it, obtained by any method including obtaining the nucleic acid from a biological source, synthesizing the nucleic acid in vitro, or amplifying the nucleic acid by any method known in the art.

As used herein, the term "hybridize" refers to process that two complementary nucleic acid strands anneal to each other under appropriately stringent conditions. Hybridizations are typically and preferably conducted with probe-length nucleic acid molecules, preferably 20-100 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "stringent hybridization conditions" as used herein refers to hybridization conditions at least as stringent as the following: hybridization in 50% formamide, 5×SSC, 50 mM NaH2PO4, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The term "amplify" with respect to nucleic acid sequences refers to methods that increase the representation of a population of nucleic acid sequences in a sample. Nucleic acid amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 Apr.;30(4):852-6, 858, 860 passim; Zhong et al., Biotechniques 2001 Apr.; 30(4):852-6, 85 passim.

As used herein, the term "test sample" refers to any liquid or solid material believed to comprise HCV nucleic acids. In preferred embodiments, a test sample is obtained from a biological source, such as cells in culture or a tissue sample from an animal, most preferably, a human. Preferred sample tissues of the instant invention include, but are not limited to, plasma, serum, whole blood, blood cells, lymphatic fluid, cerebrospinal fluid, synovial fluid, urine, saliva, and skin or other organs (e.g. biopsy material). The term "patient sample" as used herein refers to a tissue sample obtained from a human seeking diagnosis or treatment of a disease related to a HCV infection.

The term "detectable label" as used herein refers to a composition or moiety that is detectable by spectroscopic, photochemical, biochemical, immunochemical, electromagnetic radiochemical, or chemical means such as fluorescence, chemifluoresence, or chemiluminescence, or any other appropriate means. Preferred detectable labels are fluorescent dye molecules, or fluorochromes, such fluorescein, phycoerythrin, CY3, CY5, allophycocyanine, Texas Red, peridenin chlorophyll, cyanine, FAM, JOE, TAMRA, tandem conjugates such as phycoerythrin-CY5, and the like. These examples are not meant to be limiting. Methods and compositions for detectably labeling molecules, such as oligonucleotides, PNA-DNA hybrids, etc. are well known in the art. See, e.g., U.S. Pat. Nos. 6,316,230; 6,297,016; 6,316,610; 6,060,240; 6,150,107; and 6,028,290, each of which are hereby incorporated by reference in their entirety.

The term "fluorochrome" as used herein refers to a molecule that absorbs a quantum of electromagnetic radiation at one wavelength, and emits one or more photons at a different, typically longer, wavelength in response. In preferred embodiments, a fluorochrome can be a member of a pair of physically linked fluorochromes that exhibit fluorescence energy transfer. An energy transfer pair may be excited by a quantum of electromagnetic radiation at a wavelength at which the donor fluorochrome is excited; however, fluorescence from the donor fluorochrome that would be expected in the absence of the acceptor is quenched at least in part, and emission at an emission wavelength of the acceptor fluorochrome is observed.

In particularly preferred embodiments, a fluorochrome is one member of a physically linked "molecular beacon" pair. In these embodiments, the molecular beacon pair may be excited by a quantum of electromagnetic radiation at a wavelength at which a first fluorochrome member of the pair is excited; however, fluorescence from the first fluorochrome that would be expected in the absence of the second fluorochrome is quenched at least in part. Unlike energy transfer pairs, however, emission at an emission wavelength of the acceptor fluorochrome is not observed. Thus, these labels comprise a pair of dyes, one of which is referred to as a "reporter," and the second of which is referred to as a "quencher." When the two dyes are held in close proximity, such as at the ends of a nucleic acid probe, the quencher moiety prevents detection of a fluorescent signal from the reporter moiety. When the two dyes are separated, however, the fluorescent signal from the reporter moiety becomes detectable.

The term "linker" as used herein refers to one or more chemical bonds or a chemical group used to link one moiety to another, serving as a divalent bridge, where it provides a group between two other chemical moieties.

Sample Preparation:

The presence or amount of HCV nucleic acids in a sample can be determined by reverse transcribing and amplifying the target regions within the HCV gene, preferably the 5' UTR of HCV RNA. Thus, any liquid or solid material believed to comprise HCV nucleic acids can be an appropriate sample. Preferred sample tissues include plasma, serum, whole blood, blood cells, lymphatic fluid, cerebral spinal fluid, synovial fluid and others.

Such sample will often be taken from patients suspected of having HCV infection, or having a wide spectrum of liver diseases related to HCV infection. Such diseases include chronic hepatitis, cryptogenic cirrhosis, and hepatocellular carcinoma unrelated to HBV.

Nucleic acids, including the HCV sequence of interest, may be isolated from biological samples. Various commercial nucleic acid purification kits, such as QIAGEN® BioRobot™ and QIAamp® 96 VIRUS kit are known to the skilled artisan, and used to isolate nucleic acids, including the HCV sequence of interest, from samples.

Amplification of HCV Nucleic Acids of Interest:

Target samples or isolated nucleic acids may be amplified by various methods known to the skilled artisan. Preferably, RT-PCR is used to reverse transcribe and amplify HCV nucleic acids of interest. In this method, a single oligonucleotide primer binds to the nucleic acids of interest and through the reverse transcriptase activity of certain polymerases, a complementary DNA (cDNA) is produced. This primer, combined with a second oligonucleotide primer that binds to the opposite end of the cDNA, are repetitively annealed to their complementary sequences, extended by certain DNA polymerases, and heat denatured, resulting in exponential amplification of the target nucleic acid sequences. The skilled artisan is capable of designing and preparing primers that are appropriate for reverse transcribing and amplifying a target sequence. In preferred embodiment of the instant invention, primers are designed for reverse transcribing and amplifying regions within the HCV RNA 5' untranslated region (UTR) that shows sequence conservation. Suitable primers are described in U.S. Pat. No. 5,837,442, which is incorporated herein by reference.

Hybridization Probes

Oligonucleotide probes complementary and hybridizing to the amplified target HCV nucleic acids are conjugated to a detectable label. Preferably, the detectable label is a fluorescence dye. Particularly preferred are detectable labels known as "TaqMan® probes." These labels comprise a pair of dyes, one of which is referred to as a "reporter," and the second of which is referred to as a "quencher." When the two dyes are held in close proximity, such as at the ends of a nucleic acid probe, the quencher moiety prevents detection of a fluorescent signal from the reporter moiety. When the two dyes are separated, however, the fluorescent signal from the reporter moiety becomes detectable.

TaqMan® probes can be utilized during PCR, for example, by using a DNA polymerase that cleaves a probe nucleic acid if it is bound specifically to the target nucleic acid sequence. Quantitative real-time RT-PCR using enzyme rTth to reverse transcribe and PCR-amplify HCV RNA is based on detection of a fluorescent signal produced proportionally during the amplification of a PCR product. A probe is designed to anneal to the target sequence between the traditional forward and reverse primers. The probe is labeled at the 5'end with a reporter fluorochrome, and a quencher fluorochrome is added at any other position (or at the 3' end). The probe is designed to have a higher $T_m$ than the primers. As long as both fluorochromes are on the probe, the quencher molecule stops all fluorescence by the reporter. However, as rTth polymerase extends the primer, the intrinsic 5' to 3' nuclease activity of rTth degrades the probe, releasing the reporter fluorochrome. The amount of fluorescence released during the amplification cycle is proportional to the amount of product generated in each cycle. See, e.g., van Schie et al., *Biotechniques* 29: 1296-1300 (2000).

Methods for attaching detectable labels are well known in the art. For example, fluorochromes may be attached. See, e.g., Chu et al., *Methods Mol. Biol.* 26, 145-165 (1994); Hileman et al., *Bioconjug. Chem.* 5, 436-444 (1994).

Preparation of an Internal Control

As a quality control measure, an internal amplification control may be included in one or more samples to be extracted and amplified. While hybrid HCV-phage lambda nucleic acid are described herein, the skilled artisan will understand that any detectable sequence that is not derived from HCV can be used as the control sequence. A control sequence can be produced synthetically, but is preferably produced by amplifying the control sequence, e.g., lambda phage DNA, using a pair of primer sequences comprising lambda phage sequence flanked by HCV primer target sequences, one of which also contains the T7 RNA polymerase promoter sequence at its 5' end. The resulting amplicon comprises a deoxyribonucleic acid molecule which can be reverse transcribed into a ribonucleic acid molecule using commercial in vitro transcription systems known to the skilled artisan, such as the Promega Riboprobe® in vitro Transcription System. The resulting hybrid ribonucleic acid molecule is purified from its deoxyribonucleic acid predecessor using components and methods described in such systems. The resulting purified hybrid ribonucleic acids comprise a lambda phage sequence flanked by sequences that hybridize to HCV primer sequences. These controls can be mixed with sample (or purified nucleic acids isolated from the sample), and amplified with sample nucleic acids using a pair of HCV primers. If RT-PCR amplification is successful, the internal amplification control amplicons can then be detected and differentiated from HCV sequences using a probe specific to the phage sequence. Additionally, if included in the sample prior to purification of nucleic acids, the control sequences can also act as a positive purification control.

HCV Assay

In preferred embodiments, the HCV specific primers are shown in SEQ ID:1 and SEQ ID:2, although the skilled artisan will understand that other probes may be used. Stock HCV standard curve dilutions may be run simultaneously. The methods described herein can provide qualitative and quantitative results over the range of about 350 to >6,800,000 HCV IU/ml of plasma specimen.

EXAMPLES

Example 1

Sample Collection and Preparation

Serum: Blood was collected in a sterile tube without anticoagulant and allowed to clot. The serum was separated from the clot within 6 hours of collection and immediately stored at −20° or colder in a sterile screw-capped cryogenic vial. Repeated freeze-thawing should be avoided.

Plasma: Anticoagulants of ACD, PPT or EDTA were used only. If EDTA or ACD plasma was used, separated plasma within 6 hours of collection and stored at −20° or colder in a sterile screw-capped cryogenic vial. If PPT plasma was used, centrifuged plasma after 2 hours of collection and stored at −20° C. or colder for further use.

Generally, 1.0 ml (minimum 0.4 ml) of serum or plasma samples was aliquoted and stored. These samples are stable for 3 hours ambient, 1 week in the refrigerator, and 3 months frozen. For longer term storage, serum or plasma was frozen at −20° C. or colder. Frozen specimens were thawed at 20-25° C. or in water at room temperature. Self defrosting freezers were not recommended. To prevent cross contamination, no aliquot was ever returned to the original container. Repeated freeze-thawing and specimen from leaking, broken or uncapped containers were also rejected.

Example 2

Working Reagents

QIAGEN® BioRobot™ 9604 and QIAamp 96 VIRUS BioRobot™ kit were used to isolate RNA from patient specimens. All the working reagents were prepared using the methods described in the kit.

QIAGEN® Protease: The working protease solution was prepared as follows: 10 ml of protease solvent (nuclease free water containing 0.04% sodium azide provided with the kit) was added to each bottle containing 140 mg lyophilized QIAGEN® protease provided in the QIAmp® 96DNA Blood BioRobot™ Kit. The resulting solution was aliquoted (1.25 ml) into 2.0 ml Sarstedt tubes. The working solution is stable for 2 months at 2-8° C.

Working Buffer AL: Buffer AL (a low pH buffered solution containing chaotropic sale and detergent) was supplied in QIAGEN® kit. The working solution was prepared as follows: 26 ml of Buffer AL was transferred into a 50 ml conical centrifuge tube; 1 vial (1350 µg) of QIAGEN® Carrier RNA was reconstituted with 800 µL of QIAGEN® Buffer AVE; 1 tube of HCV Lambda Internal Control RNA (20 IU/µL) was thawed; and 600 µL of carrier RNA, 100 µL Internal Control RNA and 26 ml working Buffer AL were combined and mixed by gentle inversion. This solution is stable for 2.5 hours at 20-25° C.

QIAGEN® Buffer AW1: Buffer AW1 (A buffered solution containing chaotropic salt and ethanol) was supplied in the QIAGEN® kit. The working buffer AW1 was prepared as follows: 230 ml of ethanol was added to a bottle containing 175 ml of Buffer AW1 concentrate, as described on the bottle. The working Buffer AW1 is stable for 1 year after addition of Ethanol, when stored at room temperature. The working Buffer AW1 was mixed before use.

QIAGEN® Buffer AW2. Buffer AW2 (A buffered solution of chaotropic salt and ethanol) was also supplied in the QIAGEN kit. The working buffer AW2 was prepared as follows: 640 ml of absolute ethanol (96-100%) was added to a bottle containing 274 ml of Buffer AW2 concentrate, as described on the bottle. The working Buffer AW2 is stable for one year after the addition of Ethanol, when stored at room temperature. The working Buffer AW2 was mixed before use.

PolyA RNA in solution (5 mg/ml). PolyA RNA was prepared by adding 15 ml Ambion® DEPC water to 100 mg Poly A RNA in a vial, and vortexing the solution for 5 minutes. The dissolved polyA RNA solution was transferred to a 50 ml conical centrifuge tube; 5 ml Ambion® DEPC water was then added to the PolyA RNA vial again, vortexed to dissolve remaining RNA, and transferred to the same 50 ml conical centrifuge tube. The concentration of the combined PolyA RNA solution was 100 mg/20 ml or 5 mg/ml of PolyA RNA. This PolyA RNA solution was aliquoted (1 ml) in 2 ml Sartstedt screw cap tubes and labeled as "5 mg/ml Poly A RNA". It is stable for 1 year at $\leq -20°$ C.

RNA Diluent: The RNA Diluent was prepared as follows: mix 48.5 ml of Ambion DEPC water, 1 ml of previously prepared PolyA RNA (5 mg/ml) solution and 0.5 ml of 1 M Tris (pH 7.0) in a 50 ml conical centrifuge tube, and vortex for 10 seconds. The mixture was then aliquoted (1 ml) in 2 ml Sartstedt screw cap tubes and labeled as "RNA Diluent". The RNA Diluent is stable for 1 year at $\leq -20°$ C.

6-ROX solution (5 mM & 60 uM): The 6-ROX SE was purchased from Molecular Probes (5 mg, #C-6126, or equivalent). The working solution was prepared as follows: add 1600 μL DMSO to a 5 mg vial of 6-ROX SE and vigorously vortex for at least 1 minute to ensure complete solubilization. 500 μL of the dissolved solution was then aliquoted in 2 ml Sarstedt screw cap tubes. This solution is stable for 1 year at $\leq -20°$ C. The 5 mM 6-ROX solution was then diluted to 60 μM by adding 8200 μL DMSO to 100 μL of 5 mM 6-ROX.

dNTP Mixture (10 mM): 300 μL of each dATP, dCTP, dGTP, dTTP and 1800 μL Ambion® DEPC water were combined in a 15 ml conical centrifuge tube, and subsequently aliquoted 0.5 ml in Sarstedt screw cap tubes.

Primers RD1 or RD2 (100 μM): HCV specific primers RD1 and RD2 were obtained from Operon (1.0 μMole synthesis, HPLC purification). RD1 is 5'-GCA GAA AGC GTC TAG CCA TGG CGT-3' (SEQ ID NO:1). RD2 is 5'-CTC GCA AGC ACC CTA TCA GGC AGT-3' (SEQ ID NO:2).

HCV TaqMan® Master Mix This solution was prepared according to table 1 in a 15 ml conical centrifuge tube. Probe PR2 is 5'[VIC]-CCG GGA GAG CCA TAG TGG TCT GCG [TAMRA]3' (SEQ ID NO:7), used for detecting HCV nucleic acid, and probe PR4 is 5'[6FAM]-TTG GCA ACA GTG GCA TGC ACC G-[TAMRA]3' (SEQ ID NO:8), used for internal control. Probes and 6-ROX are light sensitive. The mixture was vortexed for 30 seconds and aliquoted in 2 ml of the HCV TaqMan® Mix. The mixture is stable for 1 year at $\leq -20°$ C.

TABLE 1

HCV TaqMan ® Master Mix

| Component | Final reaction concentration | Volume (μL) |
|---|---|---|
| 5× EZ Buffer | 1× | 5,000 |
| 25 mM Manganese Acetate | 2.5 mM | 2,500 |
| 100% DMSO | 7% | 1,625 |
| 10 mM dNTP | 0.3 mM | 750 |
| 100 μM RD1 primer | 0.1 μM | 25 |
| 100 μM RD2 primer | 0.25 μM | 62.5 |
| (x μM) PR2 probe | 0.2 μM | 5000/x μM* |

TABLE 1-continued

HCV TaqMan ® Master Mix

| Component | Final reaction concentration | Volume (μL) |
|---|---|---|
| (y μM) PR4 probe | 0.05 μM | 1250/y μM* |
| 60 mM 6-ROX | 300 nM | 125 |
| Water | n/a | to 10,500 |

*Probes are supplied by the manufacturer in solution with specified concentrations, indicated in the above table as "x" and "y".

The working HCV TaqMan® Master Mix for 50 reactions was then prepared by adding 200 μL rTth to 1050 μL of HCV TaqMan® Master Mix and vortexing for 3 seconds. A single reaction would contain 4 μL rTth and 21 μL of HCV TaqMan® Master Mix. The working HCV TaqMan® Master mix is stable for 2 hours at 4° C. in the dark.

Low DNA Mass Ladder (LDML) Working Reagent: 200 μL Low DNA Mass Ladder (470 ng/4 μL, Gibco BRL® Cat# 10068-013) was combined with 100 μL 6× gel loading dye and 300 μL water, labeled as LDML (470 ng/12 μL). Such a solution will be stable for 1 year at $\leq -20°$ C.

Primers LARD1 or LARD2 (50 μM): Primers LARD1 and LARD2 were used for amplifying HCV-lambda hybrids. Primer LARD1 has a sequence of 5'-TAA TAC GAC TCA CTA TAG GGG CAG AAA GCG TCT AGC CAT GGC GTA AAA TCC GGT AGT AAC TTG CTA ACC-3' (SEQ ID NO: 4). Primer LARD2 has a sequence of 5'-CTC GCA AGC ACC CTA TCA GGC AGT TAG TGC GGG TGT TGA ATG ATT TCC-3(SEQ ID NO: 5). These primers were purchased from Operon (0.2 μMole synthesis, HPLC purification).

Lambda Template DNA (10 ng/μL): 5 μg Lambda DNA (Promega, #D1501) was dissolved in Ambion® DEPC water to a final volume of 500 μL. The final concentration of the Lambda Template DNA was 10 ng/μL.

Lambda PCR Master Mix: Lambda DNA PCR Master Mix was prepared according to table 2. 50 μL of this mixture was immediately aliquoted into 0.2 ml PCR microtubes.

TABLE 2

Lambda PCR Master Mix

| Contents | Volume |
|---|---|
| 10× GeneAmp PCR Buffer II | 50 μL |
| 25 mM MgCl2 | 60 μL |
| 10 mM dNTP mixture | 15 μL |
| 50 uM Primer LARD1 | 5 μL |
| 50 uM Primer LARD2 | 5 μL |
| Water | 342.5 μL |
| AmpliTaq Gold ™ | 2.5 μL |
| Lamdba DNA (20 ng/reaction) | 20 μL |
| Total Volume (10 reactions) | 500 μL |
| Volume per reaction | 50 μL |

Example 3

Purification of HCV Lambda Internal Control DNA

HCV Lambda Internal control DNA was amplified in a PE 9600. The PCR conditions were: 95° C., hold for 9 min; 94° C., 2 temp. cycle (5×), 0.15 min, then 60° C., 0.15 min; followed by 94° C., 2 temp cycle (25×), 0.15 min, then 68° C., 0.25 min, hold at 68° C. for 10 min.

The amplified HCV Lambda Internal Control DNA was centrifuged for 5 minutes at 10,000×g. 12 μL of the reaction was used for gel analysis, and 2×245 μL of the reaction was applied to two Microcon® YM-100 purification columns (Millipore Cat#42413) pre-rinsed with 100 μL Ambion® DEPC water, and centrifuged for 5 minutes at 10,000×g. The flow-through was discarded. The wash step was repeated once. The purified HCV Lambda Internal Control DNA was eluted in 25 μL water from each column, and labeled as "LAHCV DNA". This DNA will be stable for 1 year at −20° C. Yield can be estimated/confirmed by running 2, 10 μL crude, 2 μL purified, and 4, 8, 12 μL of Low DNA Mass Ladder (LDML) working reagent on 2% gel for 20 minutes.

Example 4

Preparation of HCV Lambda Internal Control RNA & Isolation of HCV RNA

A Promega RiboProbe® Transcription system kit was used for synthesis of HCV Lambda Internal Control RNA. Basically, the following reagents were combined in order in an 0.65 ml microfuge tube: 20 μL 5× Transcription buffer, 10 μL 100 mM DTT, 2.5 μL RNasin, 5 μL each of rATP, rCTP, rGTP, rUTP, 10 μL (~1 μg) LAHCV DNA, 3 μL T7 RNA polymerase, and kit supplied nuclease free water. The total volume was 100 μL. The mixture was vortexed for 5 seconds, and then incubated 1 hour at 37° C. (heat block or programmed PE 4800 cycler). One unit (1 μL) of RNase free Dnase was then added into the mixture after the incubation, the mixture vortexed for 5 seconds, and incubated at 37° C. for 15 minutes. The mixture was then purified using phenol/chloroform by adding 100 μL of phenol/chloroform, vortexing for 15 seconds and centrifuging for 2 minutes at ≧13,000×g. The upper aqueous phase was transferred to a new tube, and 100 μL chloroform was added, followed by vortexing and centrifugation. The upper aqueous phase was transferred to a new tube, to which 2 μL (40 μg) glycogen, 10 μL 3M NaOAc (pH=5.2), and 300 μL 100% ethanol were added. The mixture was vortexed for 15 seconds and incubated at −70° C. for ≧30 minutes. After the incubation, the mixture was centrifuged at (20-25° C.) for 15 minutes at ≧13,000×g. The supernatant was removed, and 1 ml of 70% ethanol was added. The solution was mixed by gentle inversion 5 times and centrifuged at (20-25° C.) for 15 minutes at ≧13,000×g. The supernatant containing HCV Lambda Internal Control RNA was then removed and SpeedVac dried for 20 minutes (no heat). The RNA pellet was resuspended in 500 μL RNA Diluent, vortexed for 10 seconds, and held for 1 minute. Voretxing was then repeated 5 times.

RNA was isolated from patient specimens using the QIAGEN BioRobot™ 9604 and QIAamp™ 96 Virus Kit. Internal control RNA was added during the RNA isolation to enable detection of false negative results.

Example 5

Preparation of HCV RNA Positive and Negative Controls

HCV RNA Positive Control (Assay Standards): HCV RNA positive materials were thawed thoroughly. The IU/ml of positive material should be at least 5,000,000 IU/ml. Two 5 ml aliquots were prepared from the undiluted material. One of the 5 ml aliquots was thawed and the other was retained for back-up. Serial dilutions of positive material were prepared in BaseMatrix to provide 5 equally spaced (log-value) assay standards with lowest standard at a target of 350 IU/ml and highest standard representing undiluted material (or diluted to a target of <10,000,000 IU/ml). Aliquots of S1-S4 (700 μL) and S5 (1400 μL) were prepared in screw cap Sarstedt tubes and stored at −70° C. After thawing, the pilot lot of HCV RNA standards material were calibrated against WHO HCV IU/ml standard (NIBSC Cat#96/790) or secondary WHO-calibrated standard (see Calibration section below). The IU/ml of the undiluted bulk positive pool was calculated using the WHO-calibrated result. The reserved bulk positive material was thawed and mixed thoroughly. Serial dilutions were prepared using the WHO-calibrated IU/ml value in the same lot of BaseMatrix to create standards S1-S5 as described previously, labeled as HCV S1-S5, and stored at ≦−70° C. stable for 1 year.

HCV Negative Control was prepared as follows: 1 liter of BaseMatrix (BBI Cat #200158) at 2-8° C. was thawed in a secondary container for about 72 hours, mixed thoroughly, and transferred to 50 ml centrifuge tubes (~50 ml/tube). This was centrifuged at 20-25° C. for 15 minutes at 1500×g, and the supernatant transferred to clean 50 ml centrifuge tubes without disturbing pelleted material. A single use aliquot (700 μL) was prepared in screw cap Sarstedt tubes and labeled as "HCV Negative Control". Both solutions are stable for 1 year at 2-8° C.

Example 6

Calibration for Internal Control RNA and HCV Assay Standards

For HCV Internal Control RNA, the current lot was serially diluted and tested in the QIAGEN®/TaqMan® system to determine the greatest level of dilution of the primary synthesis lot that could provide consistent signal. This dilution (approximately 8 logs) of internal control in Poly A RNA carrier was assigned a value of 500 IU/ml. This assigned value was used to calculate the IU/ml equivalent concentration of the primary synthesis lot ($5 \times 10^9$ IU/μL). A single 50 μL aliquot of undiluted HCV Lambda Internal Control RNA from the current in use lot (primary synthesis lot) and the new lot to be calibrated were thawed. Serial log (1:10) dilutions were prepared of the two lots in RNA diluent (100 μL RNA+900 μL diluent).

The current lot Internal Control RNA dilutions were used as TaqMan® assay standards. Aliquots (150 μL) of the diluted internal control was prepared and labeled as "HCV TaqMan® IC". Such aliquots will be stable for 1 year at ≦−20° C.

For HCV Assay Standards, the $1^{st}$ International HCV Standard (#96/790, 50,000 IU/vial) was reconstituted to 5,000 IU/ml from the World Health Organization using BBI BaseMatrix. A single use aliquot of the International Standard material ("WHO 5000") was prepared and stored at −70° C. Three calibration runs consisting of two complete sets of the lot of TaqMan® pilot assay standards to be calibrated and four replicates of the WHO 5000 standards in each run were prepared. Preliminary values for the pilot lot of standards were calculated using the estimated value of the HCV positive material. All standards in each run were used to generate a standard curve and calculate IU/ml results for the WHO 5000 replicates. The mean result for the WHO 5000 standard (12 replicate results) was calculated. The estimated IU/ml values of the standards were multiplied by the ratio of "(5000 IU/ml)/(mean obtained IU/ml)" to calculate the WHO HCV standard-calibrated values of the pilot lot of assay standards. The values assigned to the standards were used to determine the WHO-calibrated IU/ml of the undiluted positive material. In most cases this would be the value assigned to the highest calibrator S1 (unless it was a dilution of the positive bulk). The WHO-calibrated IU/ml value assigned to the positive bulk material was used to calculate an appropriate dilution series to provide 5 equally (log value) spaced dilutions with the lowest standard at a value of 350 IU/ml.

For QIAGEN® BioRobot™ calibration and maintenance and for AB PRISM™ 7700 calibration and maintenance, it is referred to standard operation protocols known in the art.

Example 7

Quality Control Acceptance Ranges

For HCV RNA Standards, standards S1-S4 were tested in replicates of two and Standard S5 was tested in replicates of 4 in each assay run to generate a standard regression plot which was used to calculate specimen and control results in HCV IU/ml. New standard lots must be phased in against WHO-calibrated lots and produce plots with slope, intercept, and $r^2$ values within acceptance ranges (target ranges: m=−2.92 to −3.83; b =47.97 to 40.28; $r^2$ =0.964 to 1.000)

For Internal Control, HCV Lambda Internal Control RNA was added to Buffer AL before each run to monitor assay performance and guarded against false negative result reports in HCV negative specimens. Internal control lots must be phased in and demonstrate mean threshold cycle (Ct) values for at least 4 replicates over 3 separate runs within acceptance range (target range=31.42 to 36.06)

For HCV RNA Negative Control, BBI BaseMatrix was included in duplicate in each run as the negative control. BaseMatrix was confirmed as HCV negative using the HCV TMA Quantitative Assay with a sensitivity of detection to <3 IU/ml. New lots of negative control must demonstrate results of <350 IU/ml for at least 4 replicates over 3 separate runs.

For HCV RNA Positive Controls, BBI ACCURUN 305 HCV RNA Positive Control Series 400 (5 ml/pk, BBI Cat#305-5424) and BBI ACCURUN Reference 405 HCV RNA Positive Control Series 5000 (5 ml/pk, BBI Cat#A405-5024) were included in single replicates in each run to monitor assay precision and accuracy. New lots of BBI controls must have their ranges determined and were calculated as the mean ±2 SD. Target ranges may be established with less than 20 runs when approved.

For Master Mix and rTth enzyme lots, they would be phased in and meet the target acceptance ranges specified in HCV Run Standards and HCV Positive Controls. Additionally, new master mix and enzyme lot may require parallel performance tests that compare specimen results.

Example 8

Preparation for HCV Real-Time PCR and Fluorogenic Probe Hybridization

As discussed above, RNA was isolated from patient specimens using the QIAGEN® BioRobot™ and QIAamp®) 96 Virus Kit. The QIAGEN® BioRobot™ was also used to transfer specimen RNA from the BioRobot's 96-well isolation rack to the reverse transcription-PCR (RT-PCR) amplification mixture. RT-PCR amplification of the specimen RNA was performed in the presence of dual-labeled fluorescent probes in an ABI PRISM® 7700 Sequence Detection System. The amplification target is a 244 bp sequence within the highly conserved 5' untranslated region of the HCV genome. This region was the same as in the previous HCV Monitor Test Version (Young et al., *Journal of Clinical Microbiology* 31: 882-886, 1993; Roche AMPLICOR® Hepatitis C Virus (HCV) Test, version 2 Package Insert, Roche Diagnostic Systems, Branchburg N.J., 1998). The ABI PRISM®7700 instrument measures the fluorescent signals generated during the PCR (5' nuclease) process by the HCV-specific and internal control-specific probes. The amount of HCV RNA present in the specimens is calculated by comparing fluorescent signals generated by the specimens with those produced by the HCV RNA calibration standards included in the run.

In general, thawed patient specimens, controls, and standards for the run inside a Biosafety hood while the BioRobot was prepared for the run. The protocol "Ultra HCV RNA Isolation" was selected from the menu in the QIAsoft® Execute environment and The racks with aliquot tubes were placed into barcode reader rack on the BioRobot.

TABLE 3

| | QIAamp 96 plate | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 1 | 2 | 3 | 4 | 5 | 6 | 7 | 8 | 9 | 10 | S1 | S5 |
| B | 11 | 12 | 13 | 14 | 15 | 16 | 17 | 18 | 19 | 20 | S2 | S5 |
| C | 21 | 22 | 23 | 24 | 25 | 26 | 27 | 28 | 29 | 30 | S3 | B400 |
| D | 31 | 32 | 33 | 34 | 35 | 36 | 37 | 38 | 39 | 40 | S4 | neg |
| E | 41 | 42 | 43 | 44 | 45 | 46 | 47 | 48 | 49 | 50 | S1 | S5 |
| F | 51 | 52 | 53 | 54 | 55 | 56 | 57 | 58 | 59 | 60 | S2 | S5 |
| G | 61 | 62 | 63 | 64 | 65 | 66 | 67 | 68 | 69 | 70 | S3 | B5000 |
| H | 71 | 72 | 73 | 74 | 75 | 76 | 77 | 78 | 79 | 80 | S4 | neg |

There was about 1 hour before interaction was required. However, Any incompletely vacuumed lysates or washes when prompted after vacuum steps were removed and recorded. An MP-slot adapter was removed and placed in MP slot 3. The QIAamp 96 plate was then placed on top of the CMTR. Caps from Buffer AVE tubes were removed, and airpore tape was used during final centrifugation. The CMTR was covered but not capped until RNA had been added to master mix, which should be done within 1 hour of run completion, or cap and store RNA immediately at −70° C.

The isolated RNA was then transferred to the Master Mix. The working Master Mix may be prepared up to 2 hours before the start of the Automated RNA isolation and loading. In general, two tubes of working Master Mix were prepared by adding 200 μL of rTth to 1050 μL of HCV TaqMan® Master Mix, described above, vortexing 3 seconds and quickly centrifuging to settle the contents. 25 μL of working Master Mix from one tube was added to positions A1 through D12 (top half) of 96 well optical plate and 25 μL of Working Master Mix from the second tube was added to positions E1 through H12 (bottom half) of 96 well optical plate.

The isolated RNA was thawed, if stored frozen, and transferred to the Master Mix within 1 hour of thaw. The RNA was used immediately upon completion of centrifugation for HCV TaqMan® RT-PCR.

The HCV TaqMan RT-PCR was performed in ABI PRISM® 7700 and associated Macintosh G4 computer. In the Thermalcycling Conditions, stage 1 is 62° C. for 30 minutes, stage 2 is 40 cycles of 90° C. for 10 seconds and 58° C. for 25 seconds. The reaction volume was set to 50 μL. In Sample type setup, STD and UNKN reporters were selected as VIC and the IPC+ reporter was selected as FAM. All others were set to NONE. In the TrayMap FAM dye layer, all wells were set to IPC+; for VIC dye layer, all were set to UNKN except for the normal STND well positions.

Example 9

Data Analysis and Reporting

For a complete run to be accepted, all the following were required to be valid without modification: both Negative Controls<350 IU/ml with Ct values for IC<40 cycles; Low Standard: at least 2 of 4 lowest calibrator have Ct<40 cycles; Both Positive Controls>350 IU/ml and at least one of two positive controls in range. Standard Curve should have a slope of −2.92 to −3.83 and intercept of 47.97 to 40.28 with $r^2$=0.964 to 1.000.

The measurement of HCV RNA in serum and/or plasma may be used to quantitate HCV viral replication, monitor therapy and predict the success of antiviral therapy. The method used to quantitate HCV in this test is the fluorogenic 5′ nuclease (TaqMan®) RT-PCR. The test has a linear range of 350 to 6,800,000 IU/ml.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

What is claimed is:

1. An oligonucleotide having a sequence selected from the group consisting of:

```
                                                       (SEQ ID NO:4)
5'-TAA TAC GAC TCA CTA TAG GGG CAG AAA GCG TCT AGC
CAT GGC GTA AAA TCC GGT AGT AAC TTG CTA ACC-3', (SEQ ID NO:5)
5'-CTC GCA AGC ACC CTA TCA GGC AGT TAG TGC GGG TGT
TGA ATG ATT TCC-3',
and
                                                       (SEQ ID NO:6)
5'-TTG GCA ACA GTG GCA TGC ACC G-3'.
```

2. The oligonucleotide of claim 1, wherein said oligonuclotide is conjugated to a detectable label.

3. The oligonucleotide of claim 2, wherein the detectable label is a fluorescent dye.

4. The oligonucleotide of claim 2, wherein the detectable label is a fluorescent molecular beacon pair.

5. The oligonucleotide of claim 4, wherein the oligonucleotide is 5'[2'-chloro-7'-phenyl-1,4-dichloro-6-carboxyfluorescein (VIC)]-CCG GGA GAG CCA TAG TGG TCT GCG-(SEQ. ID. NO.7) [6-carboxytetramethylrhodamine (TAMRA)] 3' or 5' [6carboxyfluorescein(FAM)]-TTG GCA ACA GTG GCA TGC ACC G-(SEQ. ID. NO. 8) [6-carboxytetramethylrhodamine (TAMRA)]3'.

6. The oligonucleotide of claim 1, wherein said oligonucleotide is SEQ ID NO:4 and SEQ ID NO:5.

7. An oligonucleotide consisting of:

5'-CCG GGA GAG CCA TAG TGG TCT GCG-3' (SEQ ID NO: 3).

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcagaaagcg tctagccatg gcgt                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctcgcaagca ccctatcagg cagt                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccgggagagc catagtggtc tgcg                                           24

<210> SEQ ID NO 4
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
taatacgact cactataggg gcagaaagcg tctagccatg gcgtaaaatc cggtagtaac    60
ttgctaacc                                                            69

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctcgcaagca ccctatcagg cagttagtgc gggtgttgaa tgatttcc                 48

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttggcaacag tggcatgcac cg                                             22

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccgggagagc catagtggtc tgcg                                           24

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 8
ttggcaacag tggcatgcac cg                                              22
```